(12) United States Patent
DeAth et al.

(10) Patent No.: US 6,346,281 B1
(45) Date of Patent: Feb. 12, 2002

(54) ANTIMICROBIAL COMPOSITION FORMULATED WITH ESSENTIAL OILS

(75) Inventors: S. Samuel DeAth, Waterdown; Joy DeAth, Port Perry, both of (CA)

(73) Assignee: Scentsible Life Products, A division of Laid Back Designs Ltd., Flamborough (CA)

( * ) Notice: Subject to any disclaimer, the term of this patent is extended or adjusted under 35 U.S.C. 154(b) by 0 days.

(21) Appl. No.: 09/564,282

(22) Filed: May 5, 2000

(51) Int. Cl.[7] .......................... A61K 35/78; A01N 25/00
(52) U.S. Cl. ....................... 424/725; 424/742; 424/746; 424/405
(58) Field of Search ................................. 424/725, 742, 424/746, 405; 422/28, 36; 426/49; 429/109; 134/22.14; 510/309, 293, 295, 303, 319, 341, 372, 375, 382–383, 463, 155

(56) References Cited

U.S. PATENT DOCUMENTS

| 3,697,641 | A | * | 10/1972 | Ahrens |
| 4,748,279 | A | * | 5/1988 | Whiteley |
| 4,952,398 | A | * | 8/1990 | Tapin |
| 5,403,587 | A |   | 4/1995 | McCue et al. |
| 5,437,858 | A | * | 8/1995 | Hungerbach et al. |
| 5,716,920 | A | * | 2/1998 | Glenn, Jr. et al. |
| 6,010,933 | A | * | 1/2000 | Romano et al. |
| 6,010,993 | A | * | 1/2000 | Romano et al. |
| 6,022,459 | A | * | 2/2000 | Briggs |

FOREIGN PATENT DOCUMENTS

| CH | 688 787 | | 3/1998 |
| EP | 0842606 | | 5/1998 |
| FR | 2599026 | | 11/1987 |
| JP | 06024952 | | 1/1994 |
| WO | WO 9611694 | | 4/1996 |
| WO | WO 97/31093 | * | 8/1997 |

OTHER PUBLICATIONS

Lawless, The Illustrated Encylclopedia of Essential Oils: The complete guide to the use of oils in aromatherapy and herbalism, Element Books Limited, pp. 132,139–141 and 228, 1996.*

Shnaubelt, Advanced Aromatherapy: The essential oil therapy, Healing Arts Press, Cologne, Germany, pp. 31–41, 1998.*

* cited by examiner

Primary Examiner—Christopher R. Tate
Assistant Examiner—Michele C. Flood
(74) Attorney, Agent, or Firm—Bereskin & Parr

(57) ABSTRACT

An antimicrobial composition and more particularly a germicidal spray for sanitizing and disinfecting surfaces including leather, wood, metal, plastic and fabric, comprises a mixture of essential oils capable of being dissolved or dispersed by a solvent in a water carrier. The mixture of essential oils preferably comprises thyme, lemongrass, clove and eucalyptus. The composition may include an ionizing agent such as Blue Stone ions which speeds up the antimicrobial activity of the essential oils. The product of the invention is completely natural and non-toxic to adults and children even if swallowed.

15 Claims, No Drawings

ANTIMICROBIAL COMPOSITION FORMULATED WITH ESSENTIAL OILS

FIELD OF THE INVENTION

This invention relates to disinfecting and cleaning compositions, and more particularly, to antimicrobial compositions for disinfecting, sanitizing or cleaning porous and non-porous surfaces including plastic, metal, fabric, wood, leather and skin.

BACKGROUND OF THE INVENTION

It is now well recognized that many contagious diseases are transmitted by touching unsanitized surfaces, and that disease causing germs are able to survive on some surfaces for up to five weeks. Surfaces of concern include counters and other food preparation areas, bathroom fixtures, and toys and other surfaces accessible to children in daycare facilities, as children tend to share toys and spread germs on a seemingly continuous basis. The prevention of disease is much more effective than treatment. There is therefore a need for products which safely control germs on surfaces.

A number of products have been developed for the purpose of disinfecting and cleaning various surfaces. Many of these products use toxic, poisonous chemicals. Every year, hundreds of thousands of children are accidentally poisoned by toxic products. Some of these products are difficult and inconvenient to use. Others must be wiped off by a cloth, and cloths are sometimes often a source of more germs than those originally on the surface. There is accordingly a growing need for more natural and less toxic disinfectants.

Essential oils, i.e. volatile oils distilled or extracted from plants, are natural products known to have antimicrobial properties, and attempts have been made to formulate disinfectant solutions based upon essential oils. However, because of their hydrophobic nature, essential oils are not readily miscible in water. As a result, essential oils are often difficult to prepare in a form that will allow them to be readily incorporated into an aqueous solution.

U.S. Pat. No. 5,403,587 to McCue et al. discloses an antimicrobial composition that utilizes both a solvent and a surfactant to facilitate the formation of a homogeneous aqueous mixture of an essential oil. Although this disinfectant composition is more natural than some, it requires relatively high concentrations of a solvent and synthetic surfactant, and its efficacy is open to question. There is accordingly a need for an environmentally friendly, biodegradable, non-toxic and completely natural germicidal solution capable of being sold as a consumer product to sanitize, disinfect and clean a variety of surfaces, particularly food contact surfaces.

SUMMARY OF THE INVENTION

The present invention is directed to an aqueous antimicrobial composition for disinfecting, sanitizing or cleaning surfaces, comprising a mixture of essential oils exhibiting antimicrobial properties in a water carrier, and a solvent sufficient to form an aqueous mixture of the essential oils in the water carrier. The mixture of essential oils comprises thyme, lemongrass, clove and eucalyptus. The composition may also include a biosurfactant such as BOD or Tween-80.

The present invention is also directed to an antimicrobial composition comprising at least one essential oil exhibiting antimicrobial properties in a water carrier, a solvent, and about 1 to 1000 ppm of an ionizing agent. The ionizing agent is preferably selected from the group comprising copper sulfate, cupric carbonate and silver colloidal. Most preferably the ionizing agent is a naturally occurring ionizing agent such as Blue Stone ions.

The present invention provides for a novel and completely natural composition which exhibits disinfectant properties and eliminates or significantly reduces harmful microorganisms on surfaces to which the composition is applied. The subject composition has a neutral pH, is non-toxic and does not effect the skin, eyes, lungs or coloration of products being cleaned.

The features and advantages of composition of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE PREFERRED EMBODIMENTS

The disinfectant composition of the present invention is an all-natural, non-toxic, antimicrobial composition which may be sprayed on various surfaces to eliminate microorganisms. The composition comprises about 0.5 to 10% by volume of a mixture of essential oils capable of being dissolved or dispersed in a water carrier and exhibiting antimicrobial properties in the water carrier, and about 2 to 12% by volume of a solvent sufficient to form an aqueous solution of said essential oils in a water carrier. In a preferred embodiment, the mixture of essential oils comprises thyme, lemongrass, clove and eucalyptus.

The composition of the present invention preferably comprises about 2% to 7% by volume of the mixture of essential oils, and about 2 to 3.25% by volume of an organic solvent. The organic solvent aids in the dispersion of the essential oils into the water carrier, and increases the volatilization rate of the solution. Water is included as a carrier in a sufficient amount to make a final composition of 100% by volume. The pH of the formulation contemplated by this invention is about 6.5 to 7.5.

In one preferred embodiment, the composition of the subject invention comprises about 3% by volume of the mixture of essential oils and 2% by volume of a solvent. The solvent is preferably an organic solvent such as 95% pure grain ethyl alcohol, although other non-toxic solvents such as hexadecane, n-propanol and ethyl acetate, could be used. In this embodiment, the composition comprises about 0.50% by volume of thyme, about 0.50% by volume of lemongrass, about 1.3% by volume of clove, and about 0.75% by volume of eucalyptus. It has been found that this particular mixture of essential oils exhibits unexpectedly good disinfectant (i.e. antimicrobial) properties, once dissolved or dispersed by a solvent in the water carrier, against an unusually broad spectrum of microorganisms including bacteria, viruses, spores and protozoan parasites. The composition is stable, is effective against microorganisms, and the microorganisms do not develop resistance to the formulation over time.

The composition may also include a small amount, preferably about 0.05 to 0.5% by volume, of a non-toxic biosurfactant such as BOD™ or Tween-80™. The biosurfactant acts to help solubilize and disperse the essential oils in the water carrier.

In another preferred embodiment, the composition comprises a small amount of an ionizable agent such as copper sulfate, which is sold as Blue Stone™ ions. It has been found that a very small addition of Blue Stone ions (e.g. 10–100 ppm) produces a dramatic synergistic effect in the efficiency of the essential oil formulation. It is believed that these ions reintroduce naturally occurring groundwater ions absent from pure USP grade water, which speed up the anti microbial activity of the essential oils. Alternative ionizable agent include cupric carbonate and silver colloidal.

The composition of the invention may be formulated to be dispersed from a ready-to-use dispenser system. Due to its natural and non-toxic composition, the solution does not need to be wiped off. The resulting longer contact with the surface area bearing the microorganisms ensures a higher killing rate and continuous germ control for hours. The subject composition is also non-corrosive and biodegradable.

The composition of the present invention can be prepared by the traditional methods known to one skilled in the art. For example, the composition can be constituted by preparing an aqueous mixture of a solvent such as ethanol with essential oils. The composition is then agitated or mixed until a homogeneous solution of essential oils is generated.

The subject composition can be packaged as a ready-to-use dispenser system. The liquid solution can be dispelled from a trigger pump spray bottle and squeeze bottle or pump spray bottle to produce a spray. The composition can also be incorporated into a towelette form or a gel carrier which can then be used to treat a variety of surfaces. The towelettes can be packaged individually or in bulk for individual distribution.

The compositions of the invention are illustrated by the specific formulations described below without being limited to those formulations. The following non-limiting examples are illustrative of the present invention:

EXAMPLE 1

Antimicrobial compositions were prepared, having ingredients within the ranges specified in Table 1 as follows:

TABLE 1A

| | Ingredient Concentrations | | |
| Essential Oil | Specific Gravity [Kg/L] | Minimums [v/v %] | Maximums [v/v %] |
| --- | --- | --- | --- |
| Thyme | 0.450 | 0.25 | 2.5 |
| Lemongrass | 0.882 | 0.5 | 0.75 |
| Clove | 1.041 | 0.67 | 2.5 |
| Eucalyptus | 0.915 | 0.75 | 1.1 |
| Ethanol | 0.8101 | 2 | 3.25 |
| BOD | 1.23 | 0 | 0.5 |
| Blue Stone ions | 2.29 | 0 | 1000 ppm |

The compositions in Table 1A were used and tested in accordance with the Microbial Reduction Assay described hereinbelow, and determined to be successful at rendering a microbic culture infertile. Table 1B indicates the percentage of each essential oil that have been found to individually render a microbial culture infertile after an extended contact time.

TABLE 1B

| Essential Oil | Minimums (v/v %) |
| --- | --- |
| Thyme | .076 |
| Lemongrass | .16 |
| Clove | .19 |
| Eucalyptus | .225 |

Microbial Reduction Assay

During each run for each organism, control vials were prepared by adding 1 ml of sterile phosphate buffer to each of 3 vials containing dried cell material. In addition, 1 ml of the essential oil mix was added, to each of 10 vials containing dried cell material. All vials were exposed to the 1 ml of buffer and to the 1 ml of product for 1 hour at room temperature. Then, a sterile magnetic stirring bar and 9 ml of sterile phosphate buffer were added to each vial.

Thereafter, the liquid in each vial was analyzed by membrane filtration for its viable bacterial concentration per ml. Vials which contained disinfectant were analyzed first and then the control vials were analyzed. Serial decimal dilutions were filtered from each vial and a separate, sterile funnel was used for the analysis of the liquid in each vial. The filters were placed onto Typticase Soy Agar and the plates were incubated at 35° C. Plates were examined every 24 hours and those which failed to show growth were incubated for up to 5 days. Otherwise, colony counts were obtained after each 24 hour period of incubation and incubation continued until no change was observed in the counts from one day to the next.

EXAMPLE 2

The compositions of the subject invention were successfully tested against *Staphylococcus aureus* using the adapted Quantitative Carrier Test for Sporicides, 1995, by Dr. Susan Springthorpe and Dr. Sayed Sattar, Dept. of Microbiology and Immunology, Faculty of Medicine, University of Ottawa and with a contact time of 10 minutes. The Quantitative Carrier Test was slightly modified to evaluate bacteria rather than spores (more appropriate culturing media and methods for assessing the viability of cells, etc.). *Staphylococcus aureus* has the most resistance of the government stipulated organisms for disinfectant evaluation. The data in Table 2 show that all of the compositions with the listed essential oils exhibited antimicrobial activity by passing the test used in the evaluation of such activity. Compositions 12, 15, 17 and 20 were found to be the most effective disinfectant formulations and compositions 13, 18 and 19 were very effective.

TABLE 2

Formulations and Microbial Reduction:

| | Thyme v/v % | Lemongrass v/v % | Clove v/v % | Eucalyptus v/v % | Ethanol v/v % | BOD v/v % | Blue Stone ion ppm | Log reduction |
|---|---|---|---|---|---|---|---|---|
| 1 | 0.5 | 0.5 | 0.67 | 0.75 | 2.0 | 0.5 | 0 | 3.97 |
| 2 | 0.5 | 0.5 | 1.0 | 0.75 | 2.0 | 0.5 | 0 | 4.4 |
| 3 | 0.75 | 0.75 | 1.0 | 1.1 | 2.0 | 0.5 | 0 | 3.34 |
| 4 | 0.75 | 0.5 | 1.0 | 0.75 | 2.0 | 0.5 | 0 | 4.53 |
| 5 | 1.0 | 0.5 | 1.3 | 0.75 | 2.0 | 0.5 | 0 | 4.65 |
| 6 | 1.25 | 0.5 | 1.5 | .75 | 2.25 | 0.5 | 0 | 4.66 |
| 7 | 1.25 | 0.5 | 1.5 | 0.75 | 2.25 | 0.05 | 0 | 4.47 |
| 8 | 1.25 | 0.5 | 1.5 | 0.75 | 3.25 | 0.05 | 0 | 4.5 |
| 9 | 2.5 | 0.5 | 2.5 | 0.75 | 3.25 | 0.1 | 0 | 4.92 |
| 10 | 2.5 | 0.5 | 2.5 | 0.75 | 3.25 | 0.1 | 100 | 6.3 |
| 11 | 0.5 | 0.5 | 1.3 | 0.75 | 2.25 | 0.1 | 10 | 4.88 |
| 12 | 0.5 | 0.5 | 1.3 | 0.75 | 2.25 | 0.1 | 100 | 6.65 |
| 13 | 1.0 | 0.5 | 1.3 | 0.75 | 2.25 | 0.1 | 10 | 5.35 |
| 14 | 1.0 | 0.5 | 1.3 | 0.75 | 2.25 | 0.1 | 20 | 3.39 |
| 15 | 1.0 | 0.5 | 1.3 | 0.75 | 2.25 | 0.1 | 100 | 7.0 |
| 16 | 0.75 | 0.5 | 1.3 | 0.75 | 2.25 | 0.1 | 10 | 3.15 |
| 17 | 0.5 | 0.5 | 1.3 | 0.75 | 2.25 | 0.25 | 10 | 6.1 |
| 18 | 0.5 | 0.5 | 1.3 | 0.75 | 2.25 | 0.25 | 20 | 5.8 |
| 19 | 0.75 | 0.5 | 1.3 | 0.75 | 2.25 | 0.25 | 20 | 5.75 |
| 20 | 1.0 | 0.5 | 1.3 | 0.75 | 2.25 | 0.25 | 50 | 6.7 |
| 21 | .25 | .5 | .67 | .75 | 2.0 | 0 | 0 | 2.0 |
| 22 | .25 | .5 | .67 | .75 | 2.0 | .5 | 0 | 2.33 |

EXAMPLE 3

The data in Table 3 were generated with the Quantitative Carrier Test described herein that was approved by the Canadian General Standards Board. The organisms below represent the major structures or classifications of organisms. Many of the above kills can represent kills of other similarly structured organisms including Streptococcus or Rota virus. Composition 17 of Table 2 was used for the first three organisms, and composition 21 was used for the rest of the organisms.

TABLE 3

Quantitative Carrier Test for Disinfectants:

| ORGANISM (TYPE) | COMMON RELATED PROBLEMS | REDUCTION | CONTACT TIME |
|---|---|---|---|
| *Staphylococcus Aureus* (Bacteria +) | infections | 99.9999% | 10 minutes |
| *Salmonella* (Bacteria -) | food poisoning, typhoid, septicemia, gastroenteritis | 99.9999% | 10 minutes |
| *Pseudomonas Aeruginosa* (Bacteria) | pneumonia, urinary and nosocomial infections | 99.9999% | 10 minutes |
| *Giardia Muris* (Protozoan parasite) | diarrhea (Beaver Fever), intestinal disease, common in day care settings | 98.2% | 1 hour |
| *Aspergillus Fumigatus* (Mould) | asthma, pneumonia, infections | 100.0% | on contact |
| *Escherichia Coli* (Bacteria -) | infections, epidemic diarrhea | 100.0% | 1 hour |
| *Staphylococcus Epidermidis* (Bacteria +) | infections | 100.0% | 1 hour |
| *Candida albicans* (Yeast) | vaginitis, thrush, Athletes Foot, meningitis | 99.9% | 1 hour |
| MRSA - Methicillin-resistant *Staphylococcus Aureus* (Bacteria +) | impetigo, infections, meningitis, food poisoning | 99.9% | 1 hour |
| VRE - Vancomycin-resistant *Enterococcus faecium* (Bacteria +) | urinary, pelvic and other infections | 99.9% | 1 hour |
| MS-2 bacteriophage (Simulates viruses) | simulates Herpes, many Flu & Common Cold strains, Hepatitis | 99.9% | 6 hours |
| Cryptosporidium (Protozoan parasite) | attacks those with weak immune systems, i.e. AIDS, cancer patients | 90.0% | 12 hours |

EXAMPLE 4

Lethal Dose 50 [LD50]

A toxicity test was performed that indicates the concentration of the composition at which one-half of a rat population is killed, the results of which are shown in Table 5. The LD50 for the antimicrobial composition was greater than 36 g/kg as no harm was done to any of the subjects. The product is safer than caffeine, salt, baking soda and pure cane sugar. In addition, the composition of essential oils has a Hazard Rating for the Material Safety Data Sheet [MSDS] of 0 or zero risk under Health, Fire and Reactivity.

TABLE 4

Composition, Including Specifications and Certifications:

| Ingredient | $LD_{50}$Oral-Rat | Specifications/Certification |
|---|---|---|
| Thyme | 4.70 g/kg | British Pharmacopoeia [BP], FCC, USP |
| Lemongrass | 5.60 g/kg | Food Chemical Codex [FCC] |
| Clove | 1.37g/kg | FCC |
| Eucalyptus | 4.44 g/kg | FCC |
| Solvent[1] | 7.06 g/kg | United States Pharmacopoeia [USP], FCC |
| Biosurfactant[2] | 20 g/kg | TBA |
| Ionizing Agent | 1.5 g/kg | FCC |

[1] An organic, non-toxic solvent including grain alcohols.
[2] An organic, non-toxic biosurfactant such as BOD
[3] An ionizing agent such as Blue Stone ions.

EXAMPLE 5

While the preferred mixture of essential oils comprises thyme, lemongrass, clove, and eucalyptus, the subject composition may also include other essential oils, including sage, rosemary, garlic, savoy, orange, union, camomile, pine, sandlewood, niaouli, geranium and others. Table 5 provides examples of an efficacious concentration of each oil that individually renders a microbic culture infertile.

TABLE 5

Optional Essential Oils

| Essential Oil | v/v % | Essential Oil | v/v % | Essential Oil | v/v % |
|---|---|---|---|---|---|
| lavender | 0.5 | cinnamon | 0.17 | anise | 0.37 |
| origanum | 0.1 | aspic | 0.35 | neroli | 0.475 |
| meadowsweet | 0.33 | cumin | 0.45 | peppermint | 0.25 |
| mustard | 0.42 | lemon | 0.7 | orris | 0.38 |
| melissa | 0.52 | rose | 0.25 | birch | 0.48 |

The antimicrobial composition of the present invention is believed to have a number of advantages over the prior art. The subject composition contains a relatively low concentration of solvent. The non-corrosive nature of the subject composition makes it suitable to be used on a variety of surfaces including child high chair trays, food preparation areas including cutting boards, baby toys including in day care and doctors' offices, diaper change tables, toilet seats, pet areas, fitness centres and training salon equipment and prosthetic and orthotic materials. The subject composition is non-toxic to the surface of the skin, even when in contact with the skin for long periods of time. The antimicrobial composition will not harm eyes and is non-poisonous even if ingested by small children. The formulation has been approved by the federal Bureau of Chemical Safety for use on food contact surfaces without a rinse or wipe. The subject formulation has also been shown to have an unusually broad scope of effectiveness against a wide variety of organism structures, from simple gram negative bacteria such as E. coli to spores such as Aspergillus and protozoan parasites such as Cryptosporidium (which is resistant to 150 minutes of submersion in undiluted bleach).

While the present invention has been described with reference to what are presently considered to be the preferred embodiments, it is to be understood that the invention is not limited to these embodiments. To the contrary, the invention is intended to cover various modifications and equivalent arrangements included within the spirit and scope of the appended claims.

We claim:

1. An aqueous antimicrobial composition for disinfecting, sanitizing or cleaning surfaces comprising:

(a) about 0.5 to 10% by volume of a mixture of essential oils exhibiting antimicrobial properties in a water carrier, wherein the mixture of essential oils consists essentially of antimicrobially effective amounts of thyme oil, lemongrass oil, clove oil and eucalyptus oil;

(b) about 2 to 12% by volume of a solvent sufficient to form an aqueous mixture of the essential oils in the water carrier; and (c) sufficient water to make up to 100% by volume;

(d) wherein the composition is non-toxic.

2. The composition defined in claim 1, comprising about 2% to 7% by volume of the mixture of essential oils, and about 2 to 3.25% by volume of the solvent.

3. The composition defined in claim 1, wherein the solvent comprises ethanol.

4. The composition defined in claim 1, also comprising about 1 to 1000 ppm of an agent for introducing ions into the water, wherein the ions enhance the antimicrobial properties of the essential oils.

5. The composition defined in claim 4, wherein the ion agent is selected from the group consisting of copper sulfate, cupric carbonate and colloidal silver.

6. The composition defined in claim 4, wherein the ion agent is copper sulfate.

7. The composition defined in claim 6, wherein the ion agent comprises about 10–100 ppm of copper sulfate ions.

8. The composition defined in claim 5, wherein the surfactant comprises a biosurfactant.

9. An aqueous antimicrobial composition for disinfecting, sanitizing or cleaning surfaces comprising:

(a) about 0.5 to 10% by volume of a mixture of essential oils exhibiting antimicrobial properties in a water carrier, wherein the mixture of essential oils comprises about 0.07 to 2.5% by volume of thyme oil, about 0.16 to 0.75% by volume of lemongrass oil, about 0.20 to 2.5% by volume of clove oil, and about 0.225 to 1.1% by volume of eucalyptus oil;

(b) about 2 to 12% by volume of a solvent sufficient to form an aqueous mixture of the essential oils in the water carrier; and (c) sufficient water to make up to 100% by volume.

10. The composition defined in claim 9, wherein the mixture comprises about 0.5% by volume of thyme oil, about 0.5% by volume of lemongrass oil, about 1.3% by volume of clove oil, and about 0.75% by volume of eucalyptus oil.

11. The composition defined in claim 9, comprising about 2% to 2.25% by volume of the solvent.

12. The composition defined in claim 11, also comprising about 0.05 to 0.5% by volume of a surfactant.

13. An aqueous antimicrobial composition for disinfecting, sanitizing or cleaning surfaces, comprising:
   (a) a mixture of essential oils in a water carrier, wherein the mixture comprises about 0.07% to 1.25% by volume of thyme oil, about 0.16 to 0.75% by volume of lemongrass oil, about 0.20 to 1.5% by volume of clove oil, and about 0.225 to 1.1% percent by volume of eucalyptus oil;
   (b) about 2 to 3.25% by volume of a solvent sufficient to form an aqueous mixture of the essential oils in the water carrier; and
   (c) sufficient water to make up to 100% by volume.

14. The composition defined in claim 13, wherein the composition comprises about 1 to 1000 ppm of an ion agent for introducing ions into the water, wherein the ions enhance the antimicrobial properties of the essential oils.

15. The composition defined in claim 13, also comprising about 0.05 to 0.5% by volume of a surfactant.

* * * * *